US006667408B2

(12) United States Patent
Sasaki et al.

(10) Patent No.: US 6,667,408 B2
(45) Date of Patent: Dec. 23, 2003

(54) PROCESS FOR PREPARING CYCLIC POLYETHERS

(75) Inventors: Makoto Sasaki, Chiba (JP); Kazuo Tachibana, Chiba (JP); Haruhiko Fuwa, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/049,823

(22) PCT Filed: Mar. 9, 2001

(86) PCT No.: PCT/JP01/01872

§ 371 (c)(1), (2), (4) Date: Apr. 30, 2002

(87) PCT Pub. No.: WO01/98308
PCT Pub. Date: Dec. 27, 2001

(65) Prior Publication Data
US 2003/0100773 A1 May 29, 2003

(30) Foreign Application Priority Data

Jun. 16, 2000 (JP) ........................................ 2000-182148

(51) Int. Cl.[7] ........................ C07D 313/08; C07D 319/08

(52) U.S. Cl. ........................................................ 549/355

(58) Field of Search .......................................... 549/355

(56) References Cited

PUBLICATIONS

Sasaki et al., Tetrahedron Lett., vol. 41, No. 9, pp. 1425–1428 (2000).
Sasaki et al., Org. Lett., vol 1, No. 7, pp. 1075–1077 (1999).
Fuwa et al., Tetrahedron Lett. vol. 41, No. 43, pp. 8371–8375 (2000).
Fuwa et al., Organic Letters, vol. 3, No. 22, pp. 3549–3552 (2001).
Fuwa et al., Tetrahedron, vol. 57, pp. 3019–3033 (2001).

*Primary Examiner*—Taofiq A. Solola
(74) *Attorney, Agent, or Firm*—Wenderoth, Lind & Ponack, L.L.P.

(57) ABSTRACT

A method for the producing cyclic polyether structures at room temperature, in high yield and in a convergent manner, that may be applied to the synthesis of gambierol and ciguatoxin, without using an excessive amount of phosphate compound, alkylborane and cyclic ketene acetal phosphate are subjected to cross-coupling in the presence of a basic aqueous solution using palladium [1,1'-bis (diphenylphosphino)ferrocene] chloride as a catalyst.

11 Claims, No Drawings

PROCESS FOR PREPARING CYCLIC POLYETHERS

TECHNICAL FIELD

The invention of the present application relates to a method for producing cyclic polyether compounds. More particularly, the invention of the present application relates to a method for producing cyclic polyethers that may be used as a starting material for the synthesis of natural substances such as gambierol, at room temperature without using excess phosphate compounds.

BACKGROUND OF THE INVENTION

It has been known that marine polycyclic ethers such as ciguatoxin and gambierol act as neurotoxins and exist in fish and shellfish, causing food poisoning and red tide that deadens fish. Particularly, gambierol (compound I) is a toxin isolated from a dinoflagellate, *Gambierdiscus toxicus*, and is known to have a high toxicity of $LD_{50}$ of 50 µg/kg (mice; i.p.). The complicated steric structure of gambierol has been studied in detail using NMR and chiral anisotropic reagents (*J. Am. Chem. Soc.* 1993, 115, 361–362; *Tetrahedron Lett.* 1998, 39, 97–100)

However, because obtaining and separating natural substances such as gambierol is very difficult, detailed mechanisms of the actions of such substances at the molecular level is yet unknown. Therefore, in order to unravel the mechanism by which natural substances act as food poisoning toxins, or to develop novel methods for the detection of natural substances, a practical method for supplying such substances in quantity is thought to be essential.

The inventors have found and reported an easy method for the synthesis of giant compounds with complicated structures and molecular weights of over 1,000, in small numbers of steps, wherein alkylborane is subjected to cross-coupling with cyclic enol triflate using a palladium (O) catalyst (*Tetrahedron Letters* 39, 1998, 9027). Further, the inventors have found and provided a method for the synthesis of cyclic polyether structures in a convergent manner, which may be applied to large cyclic compounds with seven or more rings by cross-coupling alkylborane and cyclic enol phosphate in the presence of a basic aqueous solution using $Pd(PPh_3)_4$ as a catalyst (Japanese Patent Application No. 12277/2000).

However, both of those methods require the use of excess phosphate compounds and relatively high temperatures are necessary to obtain the product in high yield, making the method inefficient. Hence, a novel method for the production of cyclic polyether compounds that proceeds at low temperature and gives a high reaction yield was in demand.

The coupling reaction using a palladium catalyst (Suzuki coupling reaction) may be one of the most useful methods in organic synthesis for the production of carbon-carbon bonds. However, there are few reports on room temperature Suzuki coupling reactions (*J. Chem. Soc., Chem. Commun.* 1994, 2395; *Tetrahedron* 1997, 53, 15123–15134).

The invention of the present application has been achieved under the aforementioned circumstances and its object is to solve the problems of the prior art by providing a method for the synthesis of cyclic polyether structures at room temperature, in high yield and in a convergent manner, which may be applied to the synthesis of gambierol and ciguatoxin without the use of excess phosphate compounds.

DISCLOSURE OF THE INVENTION

In order to solve the above-described problems, the invention of the present application firstly provides A method for producing cyclic polyether compounds, comprising the cross-coupling of alkylborane and cyclic ketene acetal phosphate in the presence of a basic aqueous solution using palladium [1,1'-bis(diphenylphosphino)ferrocene] chloride as a catalyst.

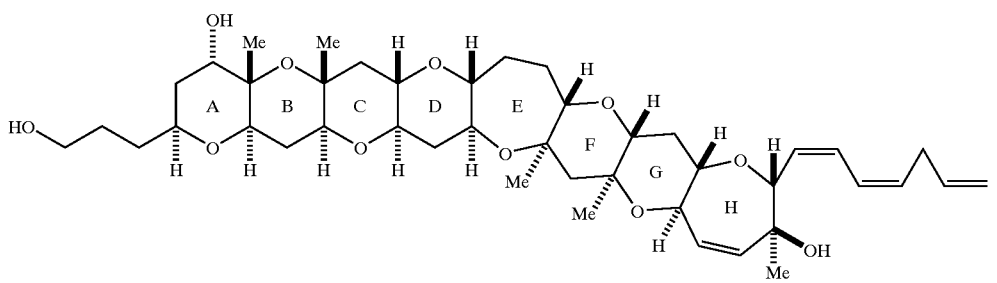

(I)

Secondly, the invention of the present application provides the method for producing cyclic polyether compounds, wherein a starting material for alkylborane and a reagent used for producing alkylborane is added to the reaction system prior to the reaction, thereby producing alkylborane in situ and cross-coupling with cyclic ketene acetal phosphate in the presence of a basic aqueous solution using palladium [1,1'-bis(diphenylphosphino)ferrocene] chloride as a catalyst; thirdly, the present invention provides the method for producing cyclic polyether compounds, wherein alkylborane is obtained by the hydroboration of exo-olefin with 9-BBN.

Fourthly the invention of the present application provides the method for producing cyclic polyether compounds, wherein the basic aqueous solution is an aqueous solution of $NaHCO_3$.

Further, fifthly, the present invention provides the method for producing cyclic polyether compounds, wherein 1 to 2 equivalents of cyclic ketene acetal phosphate is added to 1 equivalent of alkylborane.

BEST MODE FOR CARRYING OUT THE INVENTION

The method for producing cyclic polyether of the present invention is exemplified by scheme (1).

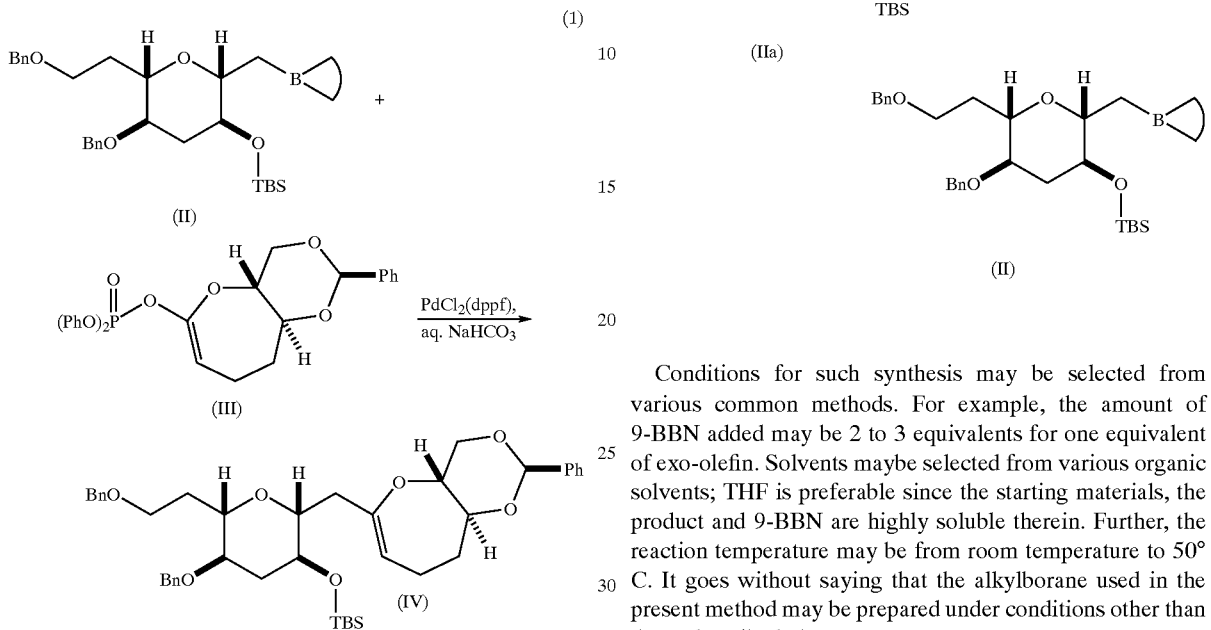

Thus, in the method for synthesizing cyclic polyether of the present invention, alkylborane (compound (II)) and cyclic ketene acetal phosphate (compound (III)) are subjected to a cross-coupling reaction in the presence of a basic aqueous solution using palladium [1,1'-bis(diphenylphosphino)ferrocene]chloride (hereinafter, referred to as "PdCl$_2$ (dppf)") as a catalyst.

In the method for synthesizing cyclic polyether of the present invention, aqueous solutions of various basic substances such as NaOH, Cs$_2$CO$_3$ and K$_3$PO$_4$ may be listed as examples of the basic aqueous solution; aqueous solution of NaHCO$_3$ is preferable, since the product may be obtained in high yield. Although the amount of the basic aqueous solution used is not particularly limited, using 3 equivalents to the exo-olefin is preferable since high yield may be obtained.

Further, the reaction temperature in not particularly limited either; in the present method for the synthesis of cyclic polyethers, the reaction yield is high even at room temperature.

Regarding the starting material, alkylborane, those of various structures may be used; as shown in scheme (2), compounds prepared by the hydroboration of oxo-olefins with 9-BBN, as disclosed in literature, are preferred.

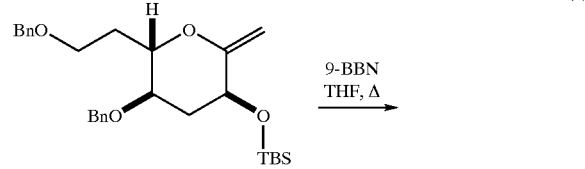

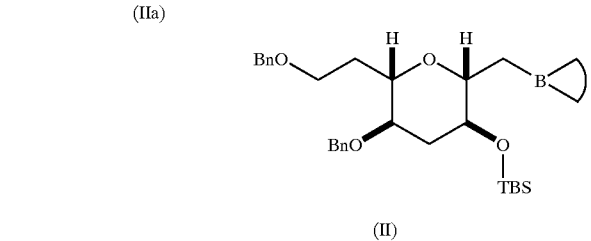

Conditions for such synthesis may be selected from various common methods. For example, the amount of 9-BBN added may be 2 to 3 equivalents for one equivalent of exo-olefin. Solvents maybe selected from various organic solvents; THF is preferable since the starting materials, the product and 9-BBN are highly soluble therein. Further, the reaction temperature may be from room temperature to 50° C. It goes without saying that the alkylborane used in the present method may be prepared under conditions other than those described above.

The exo-olefin may be selected taking in consideration the structure of the aimed product that is to be synthesized, and the reaction route by which the aimed product is prepared; an examples would be compound (IIa).

The above exo-olefin may be synthesized from alcohol by methods such as the one exemplified in scheme (3). It goes without saying that if available, a commercial substance may be used, as well.

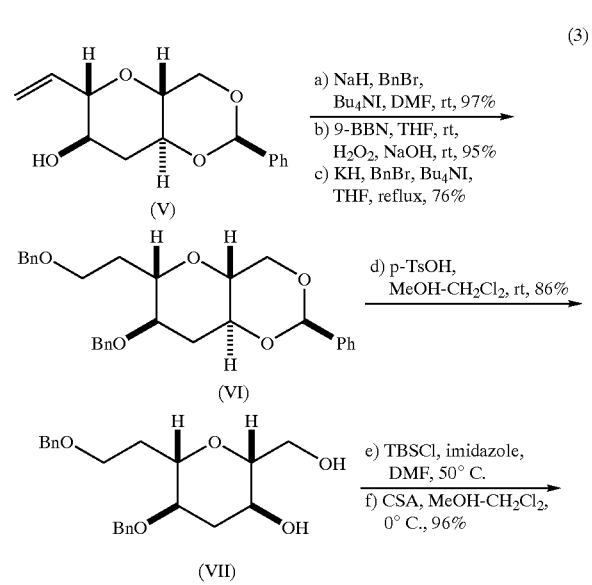

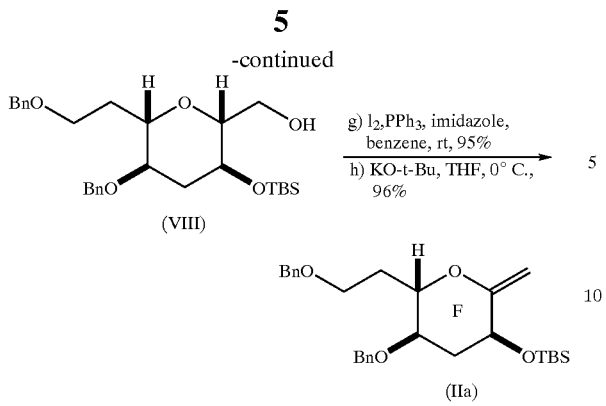

As described in the Examples to follow, the cyclic ketene acetal phosphate used in the present method for producing cyclic polyethers may be of various structures having a dihydropyran structure; each compound may be synthesized by known methods from the corresponding lactone.

In the present method for producing cyclic polyether compounds, any kind of reaction solvent may be used, as long as decomposition or the like does not occur under the reaction conditions: DMF is especially preferable. Needless to say, various solvents such as THF, methanol, acetone and water may be used for the purifying process and intermediate steps.

The reaction temperature may vary for each starting material and solvent condition; however, in the present method for producing cyclic polyethers, by using $PdCl_2$ (dppf) as a catalyst, cyclic polyethers may be obtained in high yield even at room temperature.

Furthermore, in the invention of the present application, the reaction for preparing alkylborane from exo-olefin may be carried out in situ in the reaction system where the cross-coupling of cyclic ketene acetal phosphate in the presence of a basic aqueous solution using $PdCl_2$ (dppf) as a catalyst takes place For example, exo-olefin and a reagent such as 9-BDN are added to a reaction vessel together with the cyclic ketene acetal phosphate, the basic aqueous solution and the $PdCl_2$ (dppf) catalyst to obtain a cyclic polyether compound. In the reaction system, alkylborane is first produced by the hydroboration of exo-olefin with 9-BBN and immediately subjected to cross-coupling with the cyclic ketene acetal phosphate in the reaction system, without being isolated.

In the present method for producing cyclic polyethers, when the synthesis of alkylborane is carried out in situ as described above, isolation of alkylborane, which is unstable in air, is not required; therefore, such method is preferable. Also, by synthesizing alkylborane in situ, the production process may be simplified and the amount of solvent used for the purification steps may be cut down.

It goes without saying that the method for producing cyclic polyether of the present invention may also be performed by synthesizing, purifying and separating the alkylborane first, and subjecting it to cross-coupling with the cyclic ketene acetal phosphate in the presence of a basic solution and a $PdCl_2$ (dppf) catalyst. However, as described previously, alkylborane is unstable in air, and therefore, in situ synthesis is preferable.

The invention of the present application is further described in detail by referring to the following Examples It should be understood that the invention of the present application is not limited to these Examples and that various embodiments are conceivable.

EXAMPLES

Example 1

Suzuki Coupling-Reaction of Alkylborane with Cyclic Ketene Acetal Phosphate

9-BBN (2.6 equiv) was added to exo-olefin (IIa) at room temperature and reacted in THF at room temperature. To the resulting alkylborane (II), IM aqueous solution of $NaHCO_3$ (3 equiv), $PdCl_2$ (dppf) (10 mol %) and cyclic ketene acetal phosphate (III) (1.2 equiv) was added, and the reaction was carried out in DMF at room temperature for 20 hours.

The resulting product was compound (IV) and the yield was as high as 97%.

Comparative Examples 1 to 4

Coupling Reaction of Alkylborane with Cyclic Ketene Acetal Phosphate (Comparison of Catalysts and Reaction Conditions)

The reaction was carried out as described in Example 1, using various catalyst and reaction conditions.

Comparative Example 1

First, $Pd(PPh_3)_4$ (10 mol %) was used as a catalyst and the reaction was carried out in DMF at 50° C.

Comparative Example 2

Next, the catalyst was changed to $PdCl_2$ (dppf) (10 mol %) and the reaction was carried out in DMF at 50° C.

Comparative Example 3

Further, the catalyst was changed to $PdCl_2$ $(PCY_3)_2$ (10 mol %) and the reaction was carried out in DMF at 50° C.

Comparative Example 4

Furthermore, the catalyst was changed to $Pd(OAc)_2$/o-(di-t-butylphosphino)biphenyl, which was reported as being effective in proceeding the coupling reaction in high yield at room temperature (*J. Am. Chem. Soc.* 1999, 121, 9550–9561); the reaction was carried out in dioxane at room temperature for 24 hours.

The yields of the reactions of Example 1 and Comparative Examples 1 to 4 are shown in Table 1.

TABLE 1

| | Catalyst[*1] | Reaction Conditions | Yield (%) |
|---|---|---|---|
| Example 1 | $PdCl_2$(dppf) | DMF, rt, 24 h | 97 |
| Comparative Example 1 | $Pd(PPh_3)_4$ | DMF, 50° C. 20 h | 87 |
| Comparative Example 2 | $PdCl_2$(dppf) | DMF. 50° C. 20 h | 93 |
| Comparative Example 3 | $PdCl_2(PCy_3)_2$ | DMF. 50° C. 20 h | 50 |
| Comparative[*2] Example 4 | 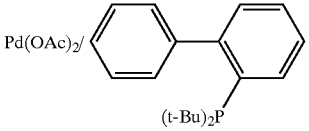 | dioxane, rt, 24 h | 58 |

[*1]catalyst: 10 mol %, $NaHCO_3$(aq.): 3 equiv., Compound (III): 1.2 equiv.
[*2]: 20 mol % ligand used From the above results, it is apparent that when $PdCl_2$(dppf) is used as a catalyst, the product is obtained in high yield even at room temperature.

Example 2

Synthesis of FGH Ring of Gambierol

The FGH ring (compound (XI)) of gambierol was synthesized according to the following scheme (4).

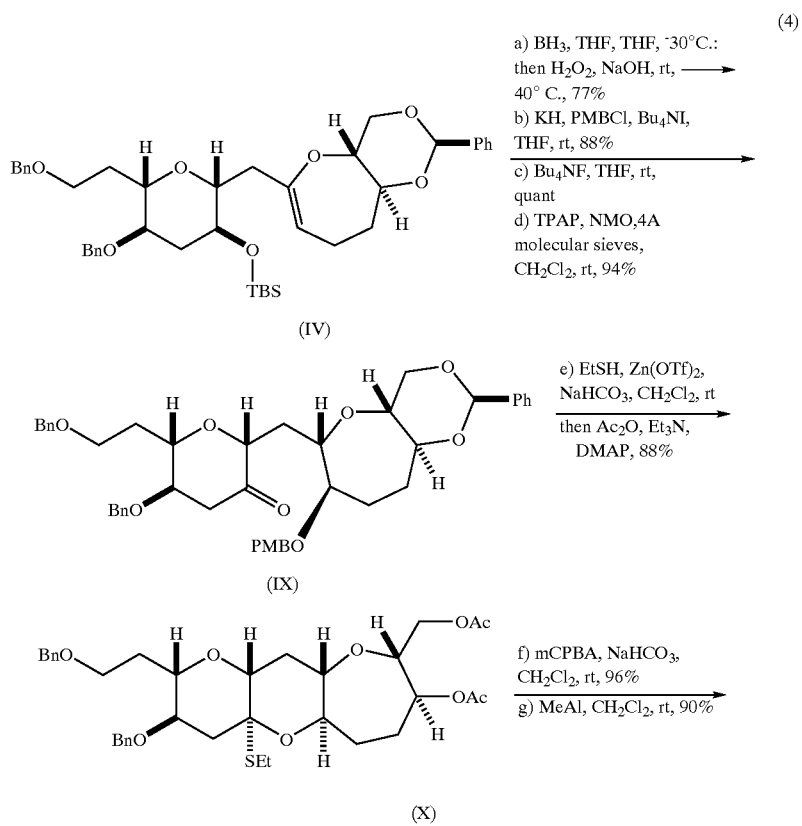

-continued

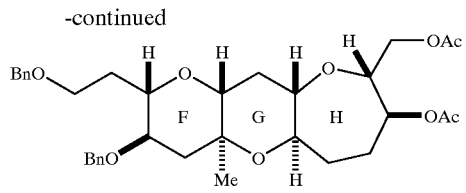

(XI)

First, the compound (IV) obtained by the method of Example 1 was hydroborated with $BH_3$ THF, and oxidized to give an alcohol (yield: 77%) stereoselectively. The alcohol was protected as a p-methoxybenzyl (PMB) ether, and desilylated, after which the resulting alcohol was oxidized with TPAP/NMO to give a ketone of compound (IX) In a yield of 83%.

Further, the PMB group was removed from the compound, reacted with EtSH and $Zn(OTf)_2$ and acetylated in situ to give a hemithioketal (X; yield: 86%).

Compound (X) was oxidized and the resulting sulfone was reacted with $Me_3Al$ to give compound (XI), the FGH ring of gambierol, in a yield of 86%.

Industrial Applicability

As described above in detail, the present invention provides a method for producing cyclic polyether structures at room temperature, in high yields, in a convergent manner, which may be applied to the synthesis of gambierol, without using an excessive amount of phosphate compounds.

What is claimed is:

1. A method for producing cyclic polyether compounds, comprising the cross-coupling reaction of alkylborane and cyclic ketene acetal phosphate in the presence of a basic aqueous solution using palladium [1,1'-bis(diphenylphosphino)ferrocene]chloride as a catalyst.

2. The method for producing cyclic polyether compounds of claim 1, wherein a starting material for alkylborane and a reagent used for producing alkylborane are added to the reaction system prior to the cross-coupling reaction, thereby producing the alkylborane in situ, which is then reacted with cyclic ketene acetal phosphate in the presence of a basic aqueous solution using palladium [1,1'-bis(diphenylphosphino)ferrocene]chloride as a catalyst.

3. The method for producing cyclic polyether compounds of claim 1, wherein the alkylborane is obtained by the hydroboration of exo-olefin with 9-BBN.

4. The method for producing cyclic polyether compounds of claim 1, wherein the basic aqueous solution is an aqueous solution of $NaHCO_3$.

5. The method for producing cyclic polyether compounds of claim 1, wherein 1 to 2 equivalents of cyclic ketene acetal phosphate are added to 1 equivalent of alkylborane.

6. The method for producing cyclic polyether compounds of claim 2, wherein the alkylborane is obtained by the hydroboration of exo-olefin with 9-BBN.

7. The method for producing cyclic polyether compounds of claim 2, wherein the basic aqueous solution is an aqueous solution of $NaHCO_3$.

8. The method for producing cyclic polyether compounds of claim 3, wherein the basic aqueous solution is an aqueous solution of $NaHCO_3$.

9. The method for producing cyclic polyether compounds of claim 2, wherein 1 to 2 equivalents of cyclic ketene acetal phosphate are added to 1 equivalent of alkylborane.

10. The method for producing cyclic polyether compounds of claim 3, wherein 1 to 2 equivalents of cyclic ketene acetal phosphate are added to 1 equivalent of alkylborane.

11. The method for producing cyclic polyether compounds of claim 4, wherein 1 to 2 equivalents of cyclic ketene acetal phosphate are added to 1 equivalent of alkylborane.

* * * * *